United States Patent [19]

Gutterer

[11] Patent Number: 5,733,901
[45] Date of Patent: Mar. 31, 1998

[54] PREDNISOLONE DERIVATIVES

[75] Inventor: Beate Gutterer, Allensbach, Germany

[73] Assignee: BYK Gulden Lomberg Chemische Fabrik GmbH, Constance, Germany

[21] Appl. No.: 530,173

[22] PCT Filed: Mar. 31, 1994

[86] PCT No.: PCT/EP94/01015

§ 371 Date: Sep. 29, 1995

§ 102(e) Date: Sep. 29, 1995

[87] PCT Pub. No.: WO94/22899

PCT Pub. Date: Oct. 13, 1994

[30] Foreign Application Priority Data

Apr. 2, 1993 [CH] Switzerland ............... 1023/93

[51] Int. Cl.$^6$ ............. C07J 71/00; A61K 31/705
[52] U.S. Cl. ............................. 514/174; 540/63
[58] Field of Search ................... 540/63; 514/174

[56] References Cited

U.S. PATENT DOCUMENTS 3,856,954 12/1974 Jackson ..................... 424/241
4,695,625 9/1987 MacDonald ..................... 540/63

Primary Examiner—Mukund J. Shah
Assistant Examiner—Pavanaram K. Sripada
Attorney, Agent, or Firm—Jacobson, Price, Holman & Stern, PLLC

[57] ABSTRACT

Epimers of the compound having the formula (I) are disclosed, both in their pure form and mixed in any desire mix ratio.

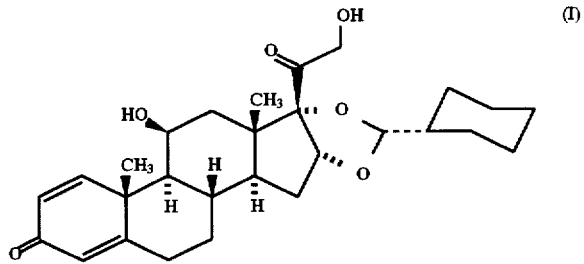

17 Claims, 1 Drawing Sheet

(I)

(Ia)

(Ib)

PREDNISOLONE DERIVATIVES

FIELD OF APPLICATION OF THE INVENTION

The invention relates to novel prednisolone derivatives which are used in the pharmaceutical industry for the production of medicaments.

KNOWN TECHNICAL BACKGROUND

DE-OS 41 29 535 discloses pregna-1,4-diene-3,20-dione-16,17-acetal-21-esters which carry a butyl, iso-propyl, sec-butyl, cyclohexyl or phenyl radical on the cyclic acetal ring, and whose C-21 hydroxyl group is acylated by an acetyl or isobutyryl radical.

DESCRIPTION OF THE INVENTION

It has now been found that the following compounds according to the invention, which differ from the compounds of DE-OS 41 29 535 by the missing acyl radical on the C-21 hydroxyl group, have surprising and advantageous properties.

DESCRIPTION OF DRAWINGS

The invention relates to the epimers of the compound of the formula I (see accompanying formula sheet) in pure form, and to mixtures of these epimers 1, 1a and 1b in any desired mixture ratio.

The epimers of the compound of the formula I can be characterized by the formulae Ia and Ib (see accompanying formula sheets).

Figure 1:
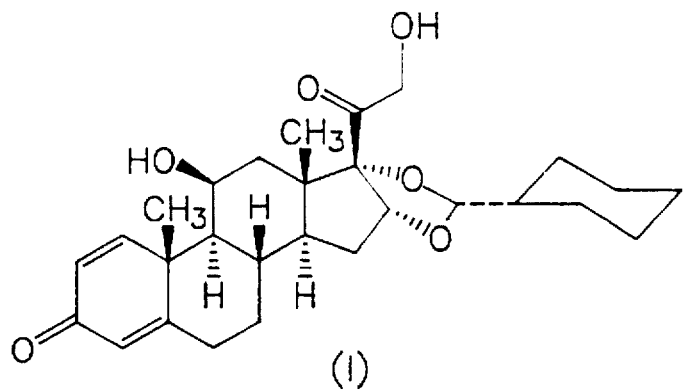
Figure 1A:
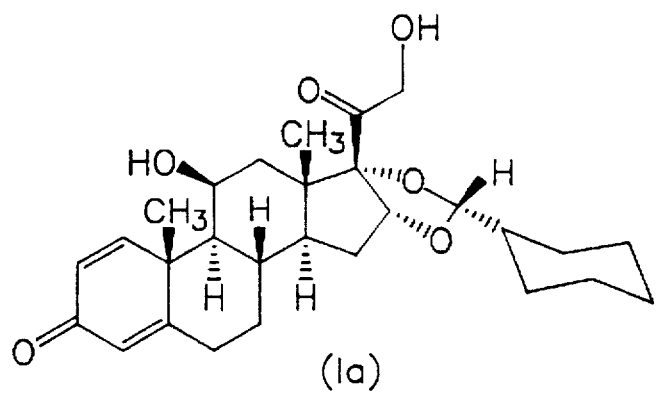
Figure 1B:
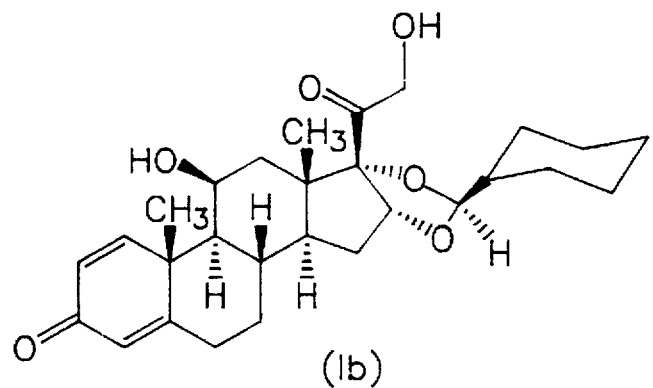

The invention further relates to a process for the preparation of the compounds according to the invention. The process comprises reacting 16-hydroxyprednisol-one with cyclohexanecarboxaldehyde.

The reaction is carried out in a manner known per se to the person skilled in the art in suitable solvents such as ethers, e.g. dioxane, diisopropyl ether; esters, e.g. ethyl acetate; halogenated hydrocarbons, e.g. methylene chloride, chloroform; nitrated hydrocarbons, e.g. nitromethane, or without solvents, with addition of catalytic or even larger amounts of acid, such as mineral acids, e.g. perchloric acid, hydrochloric acid, tetrafluoroboric acid, or sulfonic acids, e.g. methane-sulfonic acid, at temperatures of, preferably, 0° to 600° C. Preferably, the reaction to give the epimer mixture (formula I) in dioxane or ethyl acetate is carried out using 70% strength perchloric acid or 85% strength tetrafluoroboric acid at 0° C. to room temperature.

The reaction of 16-hydroxyprednisolone with cyclohexanecarboxaldehyde as a rule yields an epimer mixture, it being possible by means of suitable variation of the reaction conditions to control the reaction in such a way that a specific epimer mainly results.

To prepare mainly the R epimer (formula Ia), the following conditions, for example, are preferred: halogenated hydrocarbons or nitromethane with methane-sulfonic acid at room temperature to 40° C., or 35–70% strength perchloric acid at 0° C. to room temperature. A further possibility of preparing mainly the R epimer consists in the treatment of the epimer mixture (formula I) with 70% strength perchloric acid in a suitable solvent, e.g. methylene chloride, at 0° C. (epimerization).

Preparation mainly of the S epimer (formula Ib) is achieved with the aid of hydrogen chloride gas in a solvent such as dioxane, at 0° C. to room temperature.

If an epimer is desired in purer form than is achievable on the basis of the reaction conditions, suitable separation and purification steps, for example preparative HPLC can be added after the reaction.

The following examples serve to illustrate the invention in greater detail:

EXAMPLES 1. 500 mg (1.3 mmol) of 16-hydroxyprednisolone are suspended in 5 ml of nitromethane and treated with 33 µl (0.38 mmol) of 70% strength perchloric acid and 195 µl (1.6 mmol) of cyclohexanecarboxaldehyde. After stirring at room temperature for 4.5 h (epimer ratio in the reaction mixture R/S=55:45, HPLC content 95%), the reaction mixture is treated with sodium hydrogen carbonate solution, and the precipitate is filtered off with suction, washed with water and nitromethane and dried at 50° C. in a high vacuum. Yield: 440 mg (70%), epimer ratio R:S=57:43 (determined by means of HPLC, stationary phase ODS Hypersil, mobile phase water/ethanol=60:40).

2. 2.0 g (5.3 mmol) of 16-hydroxyprednisolone are suspended in 20 ml of nitromethane and treated with 0.88 ml (10.2 mmol) of 70% strength perchloric acid and 0.78 ml (6.4 mmol) of cyclohexanecarboxaldehyde. After stirring at room temperature for 5 h (epimer ratio in the reaction mixture R:S=73:27, HPLC content 95%), the reaction mixture is worked up as in Example 1. Yield: 1.96 g (78%), epimer ratio R:S=76:24.

3. 2.0 g (5.3 mmol) of 16-hydroxyprednisolone are suspended in 10 ml of nitromethane and 1.5 ml (17.4 mmol) of 70% strength perchloric acid and 0.8 ml (6.6 mmol) of cyclohexanecarboxaldehyde is subsequently added dropwise. The mixture is stirred at room temperature for 2 h (epimer ratio in the reaction mixture R:S=92:8, HPLC content 98%) and worked up as in Example 1. Yield: 2.2 g (88%), epimer ratio R:S=92:8.

4. 2.0 g (5.3 mmol) of 16-hydroxyprednisolone are suspended in 20 ml of nitromethane and treated with 3.52 ml (41 mmol) of 70% strength perchloric acid and 0.78 ml (6.4.mmol) of cyclohexanecarboxaldehyde. After stirring at room temperature for 1 h, the mixture is added to sodium hydrogen carbonate solution, extracted with methylene chloride, and the organic phase is dried with sodium sulfate and concentrated in vacuo. The residue is chromatographed on silica gel using methylene chloride/ethyl acetate=1:1 ($R_f$=0.5). Yield: 1.0 g (40%), epimer ratio R:S=89:11.

5. 20 g (53 mmol) of 16-hydroxyprednisolone are suspended in 300 ml of chloroform, treated with 8.0 ml (66 mmol) of cyclohexanecarboxaldehyde, and 17.6 ml (205 mmol) of 70% strength perchloric acid are added dropwise with cooling in an ice bath. After stirring at room temperature for 2.5 h, the reaction mixture is added to sodium carbonate solution, and the organic phase is extracted with water, dried using sodium sulfate and concentrated in vacuo (epimer ratio in the crude product R:S=85:15). The residue is dissolved in warm ethanol, the solution is treated with water until it becomes turbid and cooled in the ice bath, and the precipitate is filtered off with suction and dried. Yield: 20.2 g (81%), epimer ratio R:S=85:15.

6. 5.0 g (13.3 mmol) of 16-hydroxyprednisolone are suspended in 100 ml of methylene chloride, treated with 4.4 ml (51.2 mmol) of 70% strength perchloric acid and 2.1 ml (17.3 mmol) of cyclohexanecarboxaldehyde. After 1.25 h, the reaction mixture is added to sodium carbonate solution, and the organic phase is washed with water, dried using magnesium sulfate and concentrated in vacuo. Crude yield quantitative, HPLC content 96%, epimer ratio R:S=89:11.

7. 300 g (797 mmol) of 16-hydroxyprednisolone are suspended in 3.0 l of ethyl acetate, treated with 120 ml (991 mmol) of cyclohexanecarboxaldehyde and 150 ml (1.75 mol) of 70% strength perchloric acid are added dropwise in the course of 20 min. After stirring for 1 h the solution is treated with 250 g of sodium carbonate and stirred with 1.5 1 of water. The aqueous phase is extracted with ethyl acetate, and the collected organic phases with saturated sodium chloride solution. After drying the organic phase with sodium sulfate, the mixture is slowly concentrated in vacuo, and the resulting solid is filtered off with suction, washed with diethyl ether and dried. Yield: 282 g (75%), epimer ratio R:S=58:42.

8. 10.0 g (26.6 mmol) of 16-hydroxyprednisolone are suspended in 100 ml of dioxane while cooling in an ice bath, treated with 8.8 ml (102.4 mmol) of 70% strength perchloric acid and 3.7 ml (30.5 mmol) of cyclohexanecarboxaldehyde are added dropwise in the course of 45 min. The mixture is stirred at room temperature for 2 h, neutralized with sodium carbonate solution and extracted with methylene chloride. The organic phase is washed with water, dried using sodium sulfate and concentrated in vacuo (epimer ratio in the crude product R:S=49:51). The residue is taken up in warm ethanol and fractionally crystallized by adding water and cooling in an ice bath. fraction: 8.5 g, epimer ratio R:S=60:40. 2nd fraction: 2.5 g, epimer ratio R:S =27:73. Total yield: 11 g (88%).

9. 0.5 9 (1.3 mmol) of 16-hydroxyprednisolone is suspended in 20 ml of diisopropyl ether at room temperature and treated with 190 µl (1.56 mmol) of cyclohexanecarboxaldehyde and 440 µl (5.1 mmol) of 70% strength perchloric acid. After 45 min, the reaction mixture is treated with ethyl acetate and extracted with sodium hydrogen carbonate solution and water. The organic phase is dried using magnesium sulfate and concentrated in vacuo. Crude yield quantitative; HPLC content 95%, epimer ratio R:S=57:43.

10. 2.0 g (5.3 mmol) of 16-hydroxyprednisolone are suspended in 20 ml of nitromethane at room temperature and treated with 1.4 ml (21.5 mmol) of methanesulfonic acid and 0.78ml (6.4 mmol) of cyclohexanecarboxaldehyde. The solution is stirred at 40° C. for 3 h and diluted with methylene chloride after cooling. The reaction mixture is extracted with sodium hydrogen carbonate solution and water, and the organic phase is dried using sodium sulfate and concentrated in vacuo. The residue is chromatographed as in Example 4. Yield: 1.7 g (68%), epimer ratio R:S=85:15.

11. 5.0 g (13.3 mmol) of 16-hydroxyprednisolone are suspended in 50 ml of methylene chloride, treated with 3.45 ml (53.1 mmol) of methanesulfonic acid while cooling in an ice bath, and 1.95 ml (16.1 mmol) of cyclohexanecarboxaldehyde are added dropwise in the course of 10 min. The mixture is allowed to come to room temperature and is then stirred at 40° C. for 3 h. The solution is extracted with water, dried using sodium sulfate and concentrated in vacuo. Crude yield quantitative, HPLC content 96%, epimer ratio R:S= 85:15.

12. 10.0 g (26.6 mmol) of 16-hydrolxyprednisolone are suspended in 60 ml of 70% strength perchloric acid while cooling in an ice bath and treated with 3.7 ml (30.5 mmol) of cyclohexanecarboxaldehyde in the course of 10 min. After stirring for 30 minutes with ice-cooling, the mixture is added to ice-cooled sodium hydrogen carbonate solution and extracted with ethyl acetate. The organic phase is washed with sodium hydrogen carbonate solution and water, dried using sodium sulfate and concentrated in vacuo (epimer ratio in the crude product R:S=93:7). The residue is purified as in Example 8. 1st fraction: 2.1 g, epimer ratio R:S =94.5:5.5, 2nd fraction: 6.56 g, epimer ratio R:S=96:4, 3rd fraction: 1.29 g, epimer ratio R:S=91.5:8.5. Total yield: 9.95 g (79.5%).

In the case of corresponding reaction of the starting materials in 50 or 35% strength perchloric acid, an epimer ratio of R:S=95:5 or 81:19 is obtained in the crude product.

13. 5.0 g (13.3 mmol) of 16-hydroxyprednisolone are suspended in 80 ml of dioxane while cooling in an ice bath, treated with 2.5 ml of 85% strength tetrafluoroboric acid in diethyl ether, and 1.95 ml (16.1 mmol) of cyclohexanecarboxaldehyde are added in the course of 10 min. The mixture is stirred at room temperature for 1 h, then poured into sodium hydrogen carbonate solution and extracted with ethyl acetate. The organic phase is extracted with water, dried using sodium sulfate and concentrated in vacuo. The residue is chromatographed as in Example 4. Yield: 4.0 g (64%), epimer ratio R:S=47:53.

14. 100 mg (0.27 mmol) of 16-hydroxyprednisolone are suspended in 5 ml of nitromethane, treated with 50 µl of 85% strength tetrafluoroboric acid in diethyl ether and 35 µl (0.29 mmol) of cyclohexanecarboxaldehyde, and stirred at room temperature for 15 h. Epimer ratio of the reaction mixture R:S=80:20, HPLC content 96%. The adjustment of the epimer ratio can also be achieved by heating the reaction solution at 60° C. for 30 min.

15. 2.0 g (5.3 mmol) of 16-hydroxyprednisolone are suspended in 40 ml of dioxane, treated with 760 µl (6.3 mmol) of cyclohexanecarboxaldehyde while cooling in an ice bath, and 15 ml of 14.8% strength hydrogen chloride gas/dioxane solution are added dropwise in the course of 20 min. After stirring at 0° C. for 2 h and at room temperature for 2 h, the mixture is added to sodium hydrogen carbonate solution and extracted with ethyl acetate. The organic phase is washed with water, dried using sodium sulfate and concentrated in vacuo. The residue is chromatographed as in Example 4. Yield: 620 mg (25%), epimer ratio R:S=25:75.

16. 12.0 g (25.5 mmol) of 16β,17-cyclohexylmethylenedioxy-11β,21-dihydroxypregna-1,4-diene -3,20-dione (compound I, epimer ratio R:S=60:40) are dissolved in 240 ml of methylene chloride at 0° C., treated with 8.7 ml (101.1 mmol) of 70% strength perchloric acid and added to sodium hydrogen carbonate solution after stirring for 40 min. The aqueous phase is extracted with methylene chloride, and the collected organic phases are extracted with water and dried using magnesium sulfate. After concentrating the solvent in vacuo, the compound I is quantitatively recovered with an epimer ratio of R:S=90:10 (HPLC content 98%).

17. Separation of the epimers (starting from any desired epimer mixture) can be achieved with the aid of HPLC, for example as follows:

Equipment: HP 1084B liquid chromatograph, HP 79850B LC terminal and UV detector; column material: Hypersil C18, 12 µm, 250×20 mm; eluent: water (59%)/ethanol (41%); detector wavelength: 242 nm; sample concentration: 220 mg in 600 µl of DMSO+3800 µl of ethanol; application volume: 200 µl=10 mg of epimer mixture; flow rate: 10 ml/min; oven temperature: 40° C.; purity achieved: R epimer 99.6%, S epimer 99.4%.

INDUSTRIAL UTILITY

The compounds according to the invention have useful pharmacological properties, which make them industrially utilizable. They are generally suitable for the treatment of those disease conditions which can be treated by steroidal antiinflammatories. These primarily include disorders of the skin and of the respiratory tract, but also inflammatory bowel disorders and allergic rhinitis/conjunctivitis.

In the skin area, the compounds according to the invention are suitable on account of their antiinflammatory, antiproliferative, immunosuppressive, antipruriginous and vasoconstrictory properties for the (in particular topical) treatment of dermatoses of varying origin. Examples which may be mentioned are: allergic contact eczema, atopic eczema, seborrhoeic eczema, lichen simplex, psoriasis (vulgaris), sunburn, pruritus in the anogenital area, alopecia areata, hyrpertrophic scars and discoid lupus erythematosus.

In the respiratory tract area, the compounds according to the invention suppress nearly all inflammatory reactions occurring in the wall of the airways by inhibiting the proliferation, differentiation, migration and activation of the inflammatory cells and also the formation of prostaglandins, leukotrienes and PAF. As a result, the compounds according to the invention reduce bronchial hyperreactivity, decrease mucus formation, improve mucociliary clearance and potentiate (partly by increased expression of β-adrenoreceptors) the action of β-sympathomimetics. As a result of these properties, the compounds according to the invention are primarily suitable (topically applied in inhalant form) for the (long-term) therapy of bronchial asthma.

The compounds according to the invention are distinguished by a low toxicity, an essentially topical activity, a wide therapeutic spectrum, a long-lasting action and the absence of significant side effects. The activity of the compounds according to the invention makes possible their use in human and veterinary medicine.

The invention therefore further relates to a process for the treatment of mammals, including humans, who are affected by one of the abovementioned diseases. The process comprises administering to the affected mammal a therapeutically active and pharmacologically tolerable amount of one or more of the compounds according to the invention.

The invention further relates to the compounds according to the invention for use in the treatment and/or prophylaxis of said diseases.

The invention likewise relates to the use of the compounds according to the invention for the production of medicaments which are employed for the treatment and/or prophylaxis of said diseases.

The invention furthermore relates to medicaments for the treatment and/or prophylaxis of said diseases, which contain one or more of the compounds according to the invention.

For the treatment of dermatoses, the administration of the compounds according to the invention is carried out, in particular, in the form of those medicaments which are suitable for topical application. For the production of the medicaments, the compounds according to the invention (=active compounds) are preferably mixed with suitable pharmaceutical auxiliaries and additionally processed to give suitable pharmaceutical formulations. Examples of suitable pharmaceutical formulations which may be mentioned are powders, emulsions, suspensions, sprays, oils, ointments, fatty ointments, creams, pastes, gels or solutions.

On account of his expert knowledge, the person skilled in the art is familiar with the auxiliaries which are suitable for the desired pharmaceutical formulations. In addition to solvents, gel-forming agents, ointment bases and other active compound excipients, antioxidants, dispersants, emulsifiers, preservatives, solubilizers or permeation promoters can be used.

For the treatment of disorders of the respiratory tract, the compounds according to the invention are preferably applied in inhalant form. For this purpose, the latter are either administered directly as powders, (preferably in micronized form) or by atomizing solutions or suspensions which contain them. With respect to the preparations and administration forms, reference is made, for example, to the embodiments in European Patent 163 965.

The medicaments according to the invention are prepared by processes known per se. The active compounds are administered in the quantity customary for highly active glucocorticoids. Topical application forms (e.g. ointments) for the treatment of dermatoses thus contain the active compounds in a concentration of, for example, 0.1–1%. The dose for application in inhalant form is customarily between 0.2 and 2 mg per day. The customary (maintenance) dose in systemic therapy is approximately 10 mg per day, it being possible in the case of severe asthma attacks and in particular in status asthmaticus for significantly higher doses (e.g. 250–500 mg i.v.) also to be used.

PHARMACOLOGY

Experimental procedure for recording the local and systemic action of the compounds to be tested on granulation tissue formation after cotton pellet implantation in the rat (cotton pellet method):

Male Sprague-Dawley rats (in each case 8–16 animals per dose; weight per animal: 180–230 g) are each given one cotton ball (manufacturer: Hartmann, Heidenheim; cotton balls Size 2, No. 4865/2) of 13.0±0.5 mg, subcutaneously implanted bilaterally in the shoulder blade area under isofluorane anesthesia and under sterile conditions. Before the start of the experiment, alcoholic solutions (0.05 ml/pellet; 96% strength alcohol) of the compounds to be tested are in each case instilled into the cotton balls intended for implantation in the left side of the body. At the time of implantation, the pellets are dry, i.e. the substances have been deposited on the cotton fibers. The pellets on the right side of the body are implanted untreated.

In the course of 7 days, granulomas are formed as a result of foreign body irritation. On the 8th day, these are carefully excised from the sacrificed animals, i.e. with protection of the connective tissue capsule, dried (15 h at 120° C.) and weighed. By subtraction of the proportion by weight of the cotton balls, the amount of the newly formed granulation tissue is obtained.

The percentage reduction of the mean granuloma dry weight of a treated group compared with the control group (=100%) is used as a measure of the antiprolifer-drive action of a compound.

The local action of a compound is recorded on the left granulomas, and the systemic action on the right.

For recording the systemic corticoid action, the fresh weights of thymus and adrenal were also determined.

TABLE

Antiproliferative action of the compounds according to the invention after local administration in the chronic inflammation model (measured by the effect on granulation tissue formation after s.c. cotton pellet implantation (so-called cotton pellet test))

| Compound | Dose 1 × (mg per animal) Local* | Inhibition of granulation tissue formation % | p (significance) | n (number of animals) |
|---|---|---|---|---|
| Ia | 0.2 | 69 | <0.001 | 8 |
| Ib | 0.2 | 32 | <0.001 | 8 |

*Instilled into the left pellet

I claim:
1. The compound of the formula I

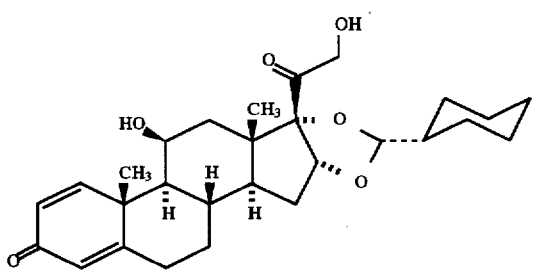

having the chemical name 16α, 17-(22R, S)-cyclohexylmethyl-enedioxy-11β, 21-dihydroxypregna-1, 4-diene -3,20-dione.

2. The compound of the formula Ia.

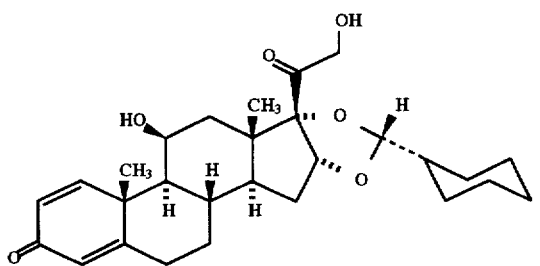

having the chemical name 16β,17-(22R)-cyclohexylmethylenedioxy-11β,21-dihydroxypregna-1,4-diene -3,20-dione.

3. The compound of the formula Ib

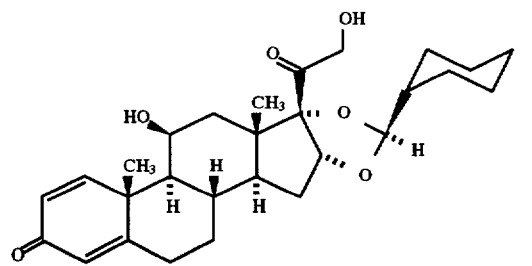

having the chemical name 16β,17-(22S)-cyclohexylmethylenedioxy-11β,21-dihydroxypregna-1,4-diene -3,20-dione.

4. A compound of formula I as claimed in claim 1, wherein the compound I is an epimer mixture of compounds Ia

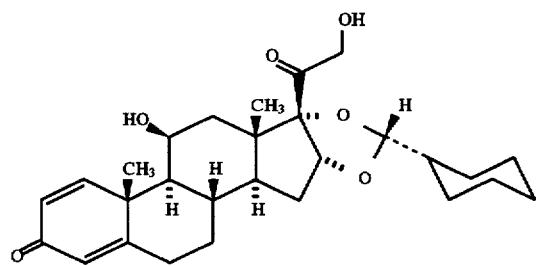

and Ib

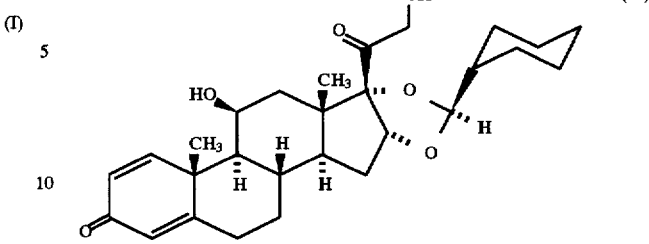

in any desired mixture ratio.

5. A process for the preparation of compound of formula I as claimed in claim 1, which comprises reacting 16-hydroxyprednisolone with cyclohexanecarboxaldehyde.

6. A pharmaceutical composition containing a suitable pharmaceutical auxiliary and a compound of formula I as claimed in claim 4 as an epimer mixture of the compounds Ia and Ib in any desired mixture ratio.

7. A pharmaceutical composition containing an inert carrier and the compound of formula Ia as claimed in claim 2.

8. A pharmaceutical composition containing an inert carrier and the compound of formula Ib as claimed in claim 3.

9. A method for treating of a disorder of the skin, a disorder of the respiratory tract, an inflammatory disorder of the bowel, or allergic rhinitis/conjunctivitis, which comprises administering an effective amount of the compound of claim 1 to a subject so affiliated.

10. A method for treating of a disorder of the skin, a disorder of the respiratory tract, an inflammatory disorder of the bowel, or allergic rhinitis/conjunctivitis, which comprises administering an effective amount of the compound of claim 2 to a subject so afflicted.

11. A method for treating of a disorder of the skin, a disorder of the respiratory tract, an inflammatory disorder of the bowel, or allergic rhinitis/conjunctivitis, which comprises administering an effective amount of the compound of claim 3 to a subject so afflicted.

12. A method for treating of a disorder of the skin, a disorder of the respiratory tract, an inflammatory disorder of the bowel, or allergic rhinitis/conjunctivitis, which comprises administering an effective amount of a compound of claim 4 to a subject so afflicted.

13. A method for producing a pharmaceutical composition with an effective amount of an active ingredient for the treatment of a disorder of the skin, a disorder of the respiratory tract, an inflammatory disorder of the bowel, or allergic rhinitis/conjunctivitis, the improvement wherein the active ingredient is the compound of claim 1.

14. A method for producing a pharmaceutical composition with an active ingredient for the treatment and/or prophylaxis of a disorder of the skin, a disorder of the respiratory tract, an inflammatory disorder of the bowel, or allergic rhinitis/conjunctivitis, the improvement wherein the active ingredient is the compound of claim 2.

15. A method for producing a pharmaceutical composition with an active ingredient for the treatment and/or prophylaxis of a disorder of the skin, a disorder of the respiratory tract, an inflammatory disorder of the bowel, or allergic rhinitis/conjunctivitis, the improvement wherein the active ingredient is the compound of claim 3.

16. A method for producing a pharmaceutical composition with an active ingredient for the treatment of a disorder of the skin, a disorder of the respiratory tract, an inflammatory disorder of the bowel, or allergic rhinitis/conjunctivitis, the improvement wherein the active ingredient is a compound of claim 4.

17. In a method for treating a disease condition which is amenable to treatment by a steroidal antiinflammatory and which comprises administering an effective amount of active ingredient to a mammal so afflicted, the improvement wherein the active ingredient comprises a member selected from the group consisting of 16β,17-(22R, S)-cyclohexylmethylenedioxy-11β,21-dihydroxypregna-1,4-diene-3,20-dione, 16β,17-(22R)-cyclohexylmethylenedioxy-11β,21-dihydroxpregna-1,4-diene-3,20-dione, and 16,α,17-(22S)-cyclohexylmethylenedioxy-11β,21-dihydroxypregna-1,4-diene-3,20-dione.

* * * * *